United States Patent
Dilk

(10) Patent No.: US 7,354,893 B2
(45) Date of Patent: Apr. 8, 2008

(54) ACETALS, USE THEREOF AS FRAGRANCES AND METHODS FOR PRODUCTION THEREOF

(75) Inventor: Erich Dilk, Holzminden (DE)

(73) Assignee: Symrise GmbH & Co., KG, Holzminden (DE)

( * ) Notice: Subject to any disclaimer, the term of this patent is extended or adjusted under 35 U.S.C. 154(b) by 206 days.

(21) Appl. No.: 10/565,510

(22) PCT Filed: Jul. 5, 2004

(86) PCT No.: PCT/EP2004/051360

§ 371 (c)(1),
(2), (4) Date: Jan. 23, 2006

(87) PCT Pub. No.: WO2005/009984

PCT Pub. Date: Feb. 3, 2005

(65) Prior Publication Data

US 2007/0014822 A1 Jan. 18, 2007

(30) Foreign Application Priority Data

Jul. 23, 2003 (DE) ................. 103 33 379

(51) Int. Cl.
*A61K 8/49* (2006.01)
*C07D 319/06* (2006.01)
*C07D 317/12* (2006.01)
(52) U.S. Cl. ............... 512/12; 549/369; 549/430
(58) Field of Classification Search ............ 549/369, 549/430; 512/12
See application file for complete search history.

(56) References Cited

U.S. PATENT DOCUMENTS 2,819,312 A * 1/1958 Isler et al. ............ 568/447

4,435,315 A  3/1984 Conrad et al.
5,753,609 A  5/1998 Nakatsu et al.

FOREIGN PATENT DOCUMENTS

WO    WO 00/04009 A    1/2000

OTHER PUBLICATIONS

Bauer, Kurt; Garbe, Dorothea; Surburg, Horst; "Common Fragrance and Flavor Materials"; 2001; Wiley-VCH Verlag GmbH.

* cited by examiner

*Primary Examiner*—Bernard Dentz
(74) *Attorney, Agent, or Firm*—Roylance, Abrams, Berdo & Goodman, L.L.P.

(57) ABSTRACT

An acetal of formula I:

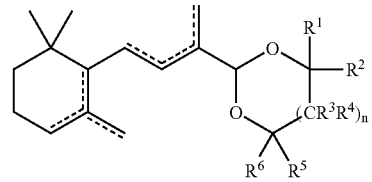

is described in which
the radicals $R^1$ to $R^6$ independently of one another are eac hydrogen, methyl, ethyl, n-propyl, isopropyl, n-butyl, isobutyl, sec-butyl or tert-butyl,
n=0 or 1, and
there is a single bond or double bond at the location of a broken line between two C atoms,
any double bond present in the chain linking the aliphatic ring to the acetal group having the E or Z configuration,
with the proviso that
the number of double bonds incorporating a C atom of the aliphatic ring is 0 or 1, and
the number of double bonds not incorporating a C atom of the aliphatic ring is 0 or 1.

12 Claims, No Drawings

ACETALS, USE THEREOF AS FRAGRANCES AND METHODS FOR PRODUCTION THEREOF

FIELD OF THE INVENTION

The present invention relates to specific acetals and acetal mixtures, to their use as fragrances, to corresponding products and to processes for their preparation.

BACKGROUND OF THE INVENTION

Because of the generally insufficient availability of many natural fragrance components, the need to adapt to changing fashions in taste, and the constantly increasing demand for novel fragrances which, on their own or in the form of compositions, constitute valuable perfumes with interesting scents, there is also a need for novel compounds with valuable fragrance qualities. Novel fragrances that are sought after in particular are compounds which, over and above their olfactory properties, have additional positive secondary properties, for example higher stability, higher strength, better lingering power, etc.

SUMMARY OF THE INVENTION

According to a first feature, the present invention relates to acetals of formula I:

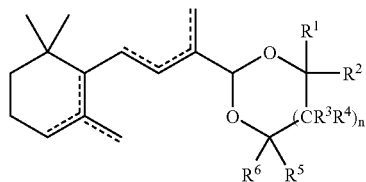

I in which
the radicals $R^1$ to $R^6$ independently of one another are each hydrogen, methyl, ethyl, n-propyl, isopropyl, n-butyl, isobutyl, sec-butyl or tert-butyl,
n=0 or 1, and
there is a single bond or double bond at the location of a broken line between two C atoms,
any double bond present in the chain linking the aliphatic ring to the acetal group having the E or Z configuration,
with the proviso that
  the number of double bonds incorporating a C atom of the aliphatic ring is 0 or 1, and
  the number of double bonds not incorporating a C atom of the aliphatic ring is 0 or 1.

Thus there can be a total of two double bonds present, of which one is allocated to the aliphatic ring (double bond in the ring or $=CH_2$ on the ring) and the other is not allocated to the ring (no C atom of the aliphatic ring is incorporated in this double bond; the double bond is located in the chain linking the aliphatic ring to the acetal group, or the chain carries a $=CH_2$ substituent) If a double bond is present in the chain linking the aliphatic ring to the acetal group, this double bond has either the E or Z configuration. Formula I thus gives no information about the E or Z configuration of such a double bond; the graphic representation shown was chosen solely for reasons of clarity and covers all the possible isomers, diastereomers and enantiomers, and especially all the possible E or Z isomers if a double bond is present in the chain linking the aliphatic ring to the acetal group.

The acetals according to the invention are particularly suitable for use as fragrances that can be used in perfume formulations. Surprisingly, the compounds according to the invention have fruity-sweet olfactory properties dominated by plum and fig notes in particular. The acetals according to the invention also have a surprisingly high and quite outstanding stability, especially in alkaline and oxidizing media. Because of these properties in particular, the acetals according to the invention are outstandingly suitable for use as fragrances, especially when they are used in a mixture of fragrances or a perfume or perfumed product which has a pH of >7 and/or an oxidizing action.

The state of the art does not disclose any olfactory descriptions for compounds that are closely structurally related to the acetals according to the invention. The following olfactory description is given for the aldehyde 2-methyl-4-(2,6,6-trimethyl-1-cyclohexen-1-yl)-2-butenal, which can be used as an educt in the preparation of the acetals according to the invention (see below) and is marketed by Symrise GmbH & Co. KG under the name "boronal": floral, with violet accents and nuances of hay, bran, leather and wood.

The compound beta-ionone, which can perhaps also be regarded as structurally similar, is described as follows in K. Bauer, D. Garbe and H. Surburg, Common Fragrance and Flavor Materials, 4th Ed., Wiley-VCH, Weinheim 2001: reminiscent of cedarwood, violet in dilution. Beta-ionone is generally regarded as a violet fragrance: violet, iris, with cedarwood nuances.

The acetals according to the invention thus have olfactory properties that are not related to those of boronal and beta-ionone.

Preferably, in the acetals according to the invention, the radicals $R^1$-$R^6$ independently of one another are each hydrogen or methyl. Particularly preferred acetals according to the invention are those of formula IA or IB below:

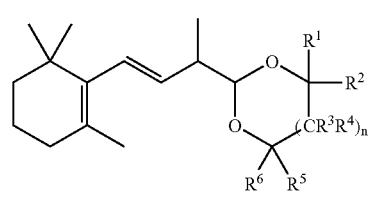

IA

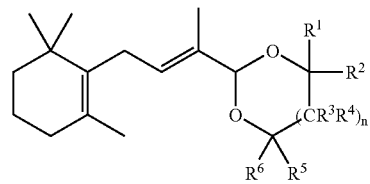

IB the double bond in the chain linking the aliphatic ring to the acetal group having the E or Z configuration in each case. The preferred meanings of the radicals $R^1$-$R^6$ are as stated above.

Very particularly preferred acetals according to the invention are 2-[1-methyl-3-(2,6,6-trimethyl-1-cyclohexen-1-yl)allyl]-1,3-dioxolane and 2-[1-methyl-3-(2,6,6-trimethyl-1-cyclohexen-1-yl)propenyl]-1,3-dioxolane.

The last-mentioned, particularly preferred acetals and other acetals according to the invention can be prepared by the acetalization of 2-methyl-4-(2,6,6-trimethyl-1-cyclohexen-1-yl)-2-butenal. Acetals according to the invention which can be obtained in this way are particularly preferred. The preferred meanings of the radicals $R^1$ -$R^6$ and the configuration of the double bond are again as stated above.

The particularly preferred acetals of formulae IA and 1B have similar olfactory notes, although the effect of the compound of formula IA is overall stronger and more impressive than that of the compound of formula IB. The acetal of formula IA is therefore particularly preferred.

The invention further relates to mixtures of two or more acetals according to the invention, all the remarks pertaining to particularly preferred acetals according to the invention also applying to the mixtures. Particularly preferred mixtures of acetals are those in which the radicals $R^1$ -$R^6$ independently of one another are each hydrogen or methyl for at least two of the acetals present. Mixtures according to the invention in which at least two of the acetals according to the invention present have formula IA or IB are also preferred.

A mixture comprising 2-[1-methyl-3-(2,6,6-trimethyl-1-cyclohexen-1-yl)allyl]-1,3-dioxolane and 2-[1-methyl-3-(2,6,6-trimethyl-1-cyclohexen-1-yl)1,3-dioxolane is very particularly preferred.

If isomers of formulae IA and IB are present together in a mixture according to the invention, it is preferable for the proportion of isomer(s) of formula IA to be greater than the proportion of isomer(s) of formula IB on account of the preferred olfactory notes of the compounds of formula IA.

If 2-[1-methyl-3-(2,6,6-trimethyl-1-cyclohexen-1-yl)allyl]-1,3-dioxolane and 2-[1-methyl-3-(2,6,6-trimethyl-1-cyclohexen-1-yl)propenyl]-1,3-dioxolane are present together in a mixture according to the invention, it is accordingly advantageous for 2-[1-methyl-3-(2,6,6-trimethyl-1-cyclohexen-1-yl)allyl]-1,3-dioxolane to be present in the larger amount.

The acetals according to the invention and mixtures thereof can be obtained by synthetic methods of organic chemistry that are known per se. It is advantageous to start from 2-methyl-4-(2,6,6-trimethyl-1-cyclohexen-1-yl)-2-butenal and convert this compound to the corresponding acetal according to the invention by reaction with an aliphatic 1,2- or 1,3-diol under acid catalysis and water separation, the substituents on the 1,2- or 1,3-diol determining the definitions of the groups $R^1$ -$R^6$ in formula I. The water formed in said reaction procedure is advantageously separated off by distillation, especially by azeotropic distillation and preferably by means of azeotropic distillation using an entraining agent so as to achieve a high product yield. Particularly suitable entraining agents are inert solvents such as toluene, xylene, cyclohexane or n-pentane.

Mixtures of acetals of formulae IA and IB according to the invention can be prepared in different proportions by choosing suitable reaction conditions or by way of transisomerization.

For example, a IA/IB isomer ratio of 6.5:1 results from the reaction of 2-methyl-4-(2,6,6-trimethyl-1-cyclohexen-1-yl)-2-butenal with ethylene glycol in toluene; because of using ethylene glycol, the compound IA corresponds in this case to 2-[1-methyl-3-(2,6,6-trimethyl-1-cyclohexen-1-yl)allyl]-1,3-dioxolane and the compound IB corresponds to 2-[1-methyl-3-(2,6,6-trimethyl-1-cyclohexen-1-yl)propenyl]-1,3-dioxolane. On the other hand, a IA/IB isomer ratio of only 2:1 results from the reaction of 2-methyl-4-(2,6,6-trimethyl-1-cyclohexen-1-yl)-2-butenal with ethylene glycol in cyclohexane. In this connection cf. also Examples 1a) and 1c) below.

The amount of acid catalyst used also influences the isomer ratio; cf. Examples 1a) and 1b) below.

A shift in the IA/IB isomer ratio from e.g. 1:2 to 10:1, i.e. in favour of the acetal of formula IA, can be achieved by heating an isomer mixture containing a high proportion of an acetal of formula IB and a lower proportion of an acetal of formula IA with p-toluenesulfonic acid in toluene, for example by way of transisomerization; in this connection cf. Example 1e) below. Other transisomerizations are also possible, depending on the particular reaction conditions.

DETAILED DESCRIPTION OF THE INVENTION

As already mentioned, the acetals according to the invention or a mixture of two or more acetals according to the invention are outstandingly suitable for use as fragrances or for the preparation of a mixture of fragrances or a perfume. The acetals or mixtures according to the invention can also advantageously be contained in products comprising a carrier or a substrate and a sensorially effective amount, in direct contact therewith, of the acetal according to the invention or the mixture of two or more acetals according to the invention.

Preferred products according to the invention are selected from the group comprising alcoholic perfumes, body care products and household cleaning or care products. Said body care products are preferably selected from the group comprising soaps, shower gels, shampoos, bath additives, skin creams, body lotions and deodorants, and said cleaning products are preferably selected from the group comprising detergents, fabric softeners, air purifiers and cleaners.

The acetals according to the invention and the mixtures according to the invention can be combined with other fragrances in different, varying proportions to form novel perfume compositions.

Examples of fragrances with which the acetals according to the invention can advantageously be combined can be found e.g. in S. Arctander, Perfume and Flavor Materials, Vol. I and II, Montclair, N.J., 1969, Selbstverlag or K. Bauer, D. Garbe and H. Surburg, Common Fragrance and Flavor Materials, 4th Ed., Wiley-VCH, Weinheim 2001.

The following may be specifically mentioned:

extracts of natural raw materials, such as ethereal oils, concrete oils, absolute essences, resins, resinoids, balsams, tinctures, e.g.:

ambergris tincture; amyris oil; angelica seed oil; angelica root oil; anise oil; baldrian oil; basil oil; tree moss absolute; bay oil; mugwort oil; benzoin resin; bergamot oil; beeswax absolute; birch tar oil; bitter almond oil; savory oil; buchu leaf oil; cabreuva oil; cade oil; calmus oil; camphor oil; cananga oil; cardamom oil; cascarilla oil; cassia oil; cassia absolute; castoreum absolute; cedar leaf oil; cedarwood oil; cistus oil; citronella oil; lemon oil; copaiva balsam; copaiva balsam oil; coriander oil; costus root oil; cumin oil; cypress oil; davana oil; dill oil; dill seed oil; eau de brouts absolute; oak moss absolute; elemi oil; tarragon oil; eucalyptus citriodora oil; eucalyptus oil; fennel oil; pine needle oil; galbanum oil; galbanum resin; geranium oil; grapefruit oil; guaiacum wood oil; gurjun balsam; gurjun balsam oil; helichrysum absolute; helichrysum oil; ginger oil; iris root absolute; iris root oil; jasmine absolute; calamus oil; blue camomile oil; Roman camomile oil; carrot seed oil; cascarilla oil; Scotch fir oil;

spearmint oil; caraway oil; ladanum oil; ladanum absolute; ladanum resin; lavandin absolute; lavandin oil; lavender absolute; lavender oil; lemongrass oil; lovage oil; distilled lime oil; pressed lime oil; linaloa oil; litsea cubeba oil; laurel leaf oil; mace oil; majoram oil; mandarin oil; massoi bark oil; mimosa absolute; ambrette oil; musk tincture; muscatel sage oil;. nutmeg oil; myrrh absolute; myrrh oil; myrtle oil; clove leaf oil; clove blossom oil; neroli oil; frankincense absolute; frankincense oil; opopanax oil; orange blossom absolute; orange oil; oreganum oil; palmarosa oil; patchouli oil; perilla oil; Peruvian balsam oil; parsley leaf oil; parsley seed oil; petitgrain oil; peppermint oil; pepper oil; pimento oil; pine oil; European pennyroyal oil; rose absolute; rosewood oil; rose oil; rosemary oil; Dalmatian sage oil; Spanish sage oil; sandalwood oil; celery seed oil; lavender spike oil; Japanese anise oil; styrax oil; tagetes oil; fir needle oil; tea tree oil; turpentine oil; thymian oil; tolu balsam; tonka absolute; tuberose absolute; vanilla extract; violet leaf absolute; verbena oil; vetiver oil; juniper oil; wine yeast oil; wormwood oil; wintergreen oil; ylang oil; hyssop oil; civet absolute; cinnamon leaf oil; cinnamon bark oil; and fractions thereof or ingredients isolated therefrom; individual fragrances from the following groups:

hydrocarbons, e.g. 3-carene; α-pinene; β-pinene; α-terpinene; γ-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane;

aliphatic alcohols, e.g. hexanol; octanol; 3-octanol; 2,6-dimethylheptanol; 2-methyl-2-heptanol; 2-methyl-2-octanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6nonadienol; 3,7-dimethyl-7-methoxyoctan-2-ol; 9-decenol; 10-undecenol; 4-methyl-3-decen-5-ol;

aliphatic aldehydes and their acetals, e.g. hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-5,9-undecadienal; heptanal diethyl acetal; 1,1-dimethoxy-2,2,5-trimethyl-4-hexene; citronellyloxyacetaldehyde;

aliphatic ketones and their oximes, e.g. 2-heptanone; 2-octanone; 3-octanone; 2-nonanone; 5-methyl-3-heptanone; 5-methyl-3-heptanone oxime; 2,4,4,7-tetramethyl-6-octen-3-one; 6-methyl-5-hepten-2-one;

aliphatic sulfur-containing compounds, e.g. 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

aliphatic nitriles, e.g. 2-nonenoic acid nitrile; 2-tridecenoic acid nitrile; 2,12-tridecadienoic acid nitrile; 3,7-dimethyl-2,6-octadienoic acid nitrile; 3,7-dimethyl-6-octenoic acid nitrile;

aliphatic carboxylic acids and their esters, e.g. (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methylpentanoate; ethyl hexanoate; allyl hexanoate; ethyl heptanoate; allyl heptanoate; ethyl octanoate; ethyl (E,Z)-2,4-decadienoate; methyl 2-octynate; methyl 2-nonynate; allyl 2-isoamyloxyacetate; methyl 3,7-dimethyl-2,6-octadienoate;

acyclic terpene alcohols, e.g. citronellol; geraniol; nerol; linalool; lavadulol; nerolidol; farnesol; tetrahydrolinalool; tetrahydrogeraniol; 2,6-dimethyl-7-octen-2-ol; 2,6-dimethyloctan-2-ol; 2-methyl-6-methylen-$^7$-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and their formates, acetates, propionates, isobutyrates, butyrates, isovalerates, pentanoates, hexanoates, crotonates, tiglates, 3-methyl-2-butenoates;

acyclic terpene aldehydes and ketones, e.g. geranial; neral; citronellal; 7-hydroxy-3,7-dimethyloctanal; 7-methoxy-3,7-dimethyloctanal; 2,6,10-trimethyl-9-undecenal; geranylacetone; and the dimethyl and diethyl acetals of geranial, neral, 7-hydroxy-3,7-dimethyloctanal;

cyclic terpene alcohols, e.g. menthol; isopulegol; alpha-terpineol; terpinen-4-ol; menthan-8-ol; menthan-1-ol; menthan-7-ol; borneol; isoborneol; linalool oxide; nopol; cedrol; ambrinol; vetiverol; guaiol; and their formates, acetates, propionates, isobutyrates, butyrates, isovalerates, pentanoates, hexanoates, crotonates, tiglates, 3-methyl-2-butenoates;

cyclic terpene aldehydes and ketones, e.g. menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8(5H)-one; nootkatone; dihydronootkatone; alpha-sinensal; betasinensal; acetylated cedarwood oil (methyl cedryl ketone);

cyclic alcohols, e.g. 4-tert-butylcyclohexanol; 3,3,5-trimethylcyclohexanol; 3-isocamphylcyclohexanol; 2,6,9-trimethyl-Z2, Z5, E9-cyclododecatrien-1-ol; 2-isobutyl-4-methyltetrahydro-2H-pyran-4-ol;

cycloaliphatic alcohols, e.g. alpha-3,3-trimethylcyclo-hexylmethanol; 2-methyl-4-(2,2,3-trimethyl-3-cyclopent-1-yl) butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

cyclic and cycloaliphatic ethers, e.g. cineol; cedryl methyl ether; cyclododecyl methyl ether; (ethoxy-methoxy)cyclododecane; alpha-cedrene epoxide; 3a,6,6,9a-tetramethyldodecahydronaphtho[2,1-b]furan; 3a-ethyl-6,6,9a-trimethyldodecahydronaphtho[2,1-b]-furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methylpropyl)-1,3-dioxane;

cyclic and macrocyclic ketones, e.g. 4-tert-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopenta-decanone; 4-(1-ethoxyvinyl)-3,3,5,5-tetramethylcyclo-hexanone; 4-tert-pentylcyclohexanone; 5-cyclohexadecen-1- one; 6,7-dihydro-1,1,2,3,3-pentamethyl-4(5H)-indanone; 8-cyclohexadecen-1-one; 9-cycloheptadecen-1-one; cyclopentadecanone; cyclohexadecanone;

cycloaliphatic aldehydes, e.g. 2,4-dimethyl-3-cyclohexenecarbaldehyde; 2-methyl-4-(2,2,6-trimethyl-cyclohexen-1-yl)-2-butenal; 4-(4-hydroxy-4-methyl-pentyl)-3-cyclohexenecarbaldehyde; 4-(4-methyl-3-penten-1-yl)-3-cyclohexenecarbaldehyde;

cycloaliphatic ketones, e.g. 1-(3,3-dimethylcyclo-hexyl)-4-penten-1-one; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl 2,6,10-trimethyl-2,5,9-cyclododecatrienyl ketone; tert-butyl 2,4-dimethyl-3-cyclohexen-1-yl ketone;

esters of cyclic alcohols, e.g. 2-tertbutylcyclohexyl acetate; 4-tert-butylcyclohexyl acetate; 2-tertpentylcyclohexyl acetate; 4-tert-pentylcyclohexyl acetate; decahydro-2-naphthyl acetate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5- or 6-indenyl acetate; 4,7-methano-3a,4,5,6,7,7a-hexahydro-5- or 6-indenyl propionate; 4,7-methano-3a,4,5,6,7,7a-hexahydro-5- or 6-indenyl isobutyrate; 4,7-methanooctahydro-5- or 6-indenyl acetate;

esters of cycloaliphatic carboxylic acids, e.g. allyl 3-cyclohexylpropionate; allyl cyclohexyloxyacetate; cis- and trans-methyl dihydrojasmonate; cis- and transmethyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxolan-2-acetate;

araliphatic alcohols, e.g. benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)-propanol; 1,1-dimethyl-2-phenylethyl alcohol; 1,1-dimethyl-3-phenylpropanol; 1-ethyl-1-methyl-3-phenyl-propanol; 2-methyl-5-phenylpentanol; 3-methyl-5-phenyl-pentanol; 3-phenyl-2-propen-1-ol; 4-methoxybenzyl alcohol; 1-(4-isopropylphenyl)ethanol;

esters of araliphatic alcohols and aliphatic carboxylic acids, e.g. benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethyl-phenylethyl acetate; alpha,alpha-dimethylphenylethyl butyrate; cinnamyl acetate; 2-phenoxyethyl isobutyrate; 4-methoxybenzyl acetate;

araliphatic ethers, e.g. 2-phenylethyl methyl ether; 2-phenylethyl isoamyl ether; 2-phenylethyl l-ethoxyethyl ether; phenylacetaldehyde dimethyl acetal; phenyl-acetaldehyde diethyl acetal; hydratropaldehyde dimethyl acetal; phenylacetaldehyde glyceryl acetal; 2,4,6-trimethyl-4-phenyl-1,3-dioxane; 4,4a,5,9b-tetrahydro-indeno[1, 2-d]-m-dioxin; 4,4a,5,9b-tetrahydro-2,4-dimethylindeno[1,2-d]-m-dioxin;

aromatic and araliphatic aldehydes, e.g. benzaldehyde; phenylacetaldehyde; 3-phenylpropanal; hydratrop-aldehyde; 4-methylbenzaldehyde; 4-methylphenyl-acetaldehyde; 3-(4-ethylphenyl)-2,2-dimethylpropanal; 2-methyl-3-(4-isopropylphenyl)propanal; 2-methyl-3-(4-tert-butylphenyl)propanal; 3-(4-tert-butylphenyl)-propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxy-benzaldehyde; 3,4-methylenedioxybenzaldehyde; 3,4-dimethoxybenzaldehyde; 2-methyl-3-(4-methoxyphenyl)-propanal; 2-methyl-3-(4-methylenedioxyphenyl)propanal;

aromatic and araliphatic ketones, e.g. acetophenone; 4-methylacetophenone; 4-methoxyacetophenone; 4-tert-butyl-2,6-dimethylacetophenone; 4-phenyl-2-butanone; 4-(4-hydroxyphenyl)-2-butanone; 1-(2-naphthalenyl)-ethanone; benzophenone; 1,1,2,3,3,6-hexamethyl-5-indanyl methyl ketone; 6-tert-butyl-1, 1-dimethyl-4-indanyl methyl ketone; 1-[2,3-dihydro-1,1,2,6-tetramethyl-3-(1-methylethyl)-1H-5-indenyl]ethanone; 5', 6', 7', 8'-tetrahydro-3', 5', 5', 6', 8', 8'-hexamethyl-2/-acetonaphthone;

aromatic and araliphatic carboxylic acids and their esters, e.g. benzoic acid; phenylacetic acid; methyl benzoate; ethyl benzoate; hexyl benzoate; benzyl benzoate; methylphenyl acetate; ethylphenyl acetate; geranylphenyl acetate; phenylethylphenyl acetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; ethyl 3-methyl-3-phenylglycidate;

aromatic nitrogen-containing compounds, e.g. 2,4,6-trinitro-1,3-dimethyl-5-tert-butylbenzene; 3,5-dinitro-2,6-dimethyl-4-tert-butylacetophenone; cinnamic acid nitrile; 5-phenyl-3-methyl-2-pentenoic acid nitrile; 5-phenyl-3-methylpentanoic acid nitrile; methyl anthranilate; methyl N-methylanthranilate; Schiff bases of methyl anthranilate with 7-hydroxy-3,7-dimethyl-octanal, 2-methyl-3-(4-tert-butylphenyl)propanal or 2,4-dimethyl-3-cyclohexenecarbaldehyde; 6-isopropyl-quinoline; 6-isobutylquinoline; 6-sec-butylquinoline; indole; skatole; 2-methoxy-3-isopropylpyrazine; 2-isobutyl-3-methoxypyrazine;

phenols, phenyl ethers and phenyl esters, e.g. estragole; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresylphenyl acetate;

heterocyclic compounds, e.g. 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

lactones, e.g. 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 1,15-pentadecanolide; cis- and trans-11-pentadecen-1,15-olide; cis- and trans-12-pentadecen-1, 15-olide; 1,16-hexadecanolide; 9-hexadecen-1,16olide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; coumarin; 2,3-dihydrocoumarin; octahydrocoumarin.

The total amount of acetals according to the invention used in perfume compositions is advantageously 0.05 to 50 wt. %, preferably 0.5 to 20 wt. %, based on the total perfume oil composition.

Perfume oils containing acetals according to the invention can be used for perfume formulations in liquid form, either undiluted or diluted with a solvent. Examples of suitable solvents for this purpose are ethanol, isopropanol, diethylene glycol monoethyl ether, glycerol, propylene glycol, 1,2- butylene glycol, dipropylene glycol, diethyl phthalate, triethyl citrate, isopropyl myristate, etc.

Perfume oils containing acetals according to the invention can also be adsorbed on a carrier to ensure both a fine distribution of the fragrances in the product and a controlled release when used. Such carriers can be porous inorganic materials, such as light sulfate, silica gels, zeolites, gypsums, clays, clay granules, gas concrete, etc., or organic materials, such as woods and cellulose-based substances.

Perfume oils containing acetals according to the invention can also be microencapsulated or spray-dried or in the form of inclusion complexes or extrusion products, and can be added in this form to the product to be perfumed.

Optionally the properties of the perfume oils modified in this way can be further optimized, in respect of a more specific perfume release, by coating with suitable materials; waxy plastics, e.g. polyvinyl alcohol, are preferably used for this purpose.

Microencapsulation of the perfume oils can be effected for example by the so-called coacervation process with the aid of capsule materials made e.g. of polyurethane-like substances or soft gelatin. Spray-dried perfume oils can be prepared for example by spray drying an emulsion or dispersion containing the perfume oil, it being possible for modified starches, proteins, dextrin and vegetable gums to be used as carriers. Inclusion complexes can be prepared for example by introducing dispersions of the perfume oil and cyclodextrins or urea derivatives into a suitable solvent, e.g. water. Extrusion products can be prepared by melting the perfume oils with a suitable waxy substance and by extrusion with subsequent solidification, optionally in a suitable solvent, e.g. isopropanol.

Perfume oils containing acetals according to the invention can be used in concentrated form, in solution or in a modified form described above for the preparation of e.g. perfume extracts, eaux de parfum, eaux de toilette, aftershave lotions, eaux de Cologne, pre-shave products, splash colognes and perfumed refreshing tissues, and for the perfuming of acidic, alkaline and neutral cleaning products, e.g. floor cleaners, window cleaners, dishwasher detergent, bath and sanitaryware cleaners, scouring cream, solid and liquid WC cleaners, carpet cleaning powders and foams, liquid detergents, powder detergents, fabric preconditioners such as bleach, soaker and stain removers, fabric softeners, washing soaps, washing tablets, disinfectants, surface disinfectants, air purifiers in liquid or gel form or applied to a solid carrier, aerosol sprays, waxes and polishes, such as furniture polishes, floor waxes and shoe polishes, body care products, e.g. solid and liquid soaps, shower gels, shampoos, shaving soaps, shaving foams, bath oils, cosmetic emulsions of the oil-in-water, water-in-oil and water-in-oil-in-water type, such as skin creams and lotions, face creams and lotions, sun creams and lotions, after-sun creams and lotions, hand creams and lotions, foot creams and lotions, depilatory creams and lotions, after-shave creams and lotions, tanning creams and lotions, hair care products, e.g. hair sprays, hair gels, strengthening hair lotions, hair rinses, permanent and semipermanent hair dyes, hair styling products, such as cold waving and straightening products, hair tonics, hair creams and lotions, deodorants and antiperspirants, e.g. armpit sprays, roll-ons, deodorant sticks and deodorant creams, decorative cosmetic products, e.g. eye shadows, nail varnishes, make-ups, lipsticks and mascara, and candles, lamp oils, incense sticks, insecticides, repellents and propellants.

The Examples which follow will illustrate the invention in greater detail (in its various features):

EXAMPLES

Example 1

Preparation of an isomer mixture of 2-[1-methyl-3-(2,6,6-trimethyl-1-cyclohexen-1-yl)allyl]-1,3-dioxolane (isomer 1) and 2-[1-methyl-3-(2,6,6-trimethyl-1-cyclohexen-1-yl)propenyl]-1,3-dioxolane (isomer 2)

a) Reaction parameters: entraining agent: toluene;
amount of p-toluenesulfonic acid =1 g Molar ratio 2-methyl-4-(2,6,6-trimethyl-1-cyclohexen-1-yl)-2-butenal: ethylene glycol =1:3

103 g (0.5 mol) of 2-methyl-4-(2,6,6-trimethyl-1-cyclohexen-1-yl)-2-butenal, 93 g (1.5 mol) of ethylene glycol and 1 g of p-toluenesulfonic acid are heated with 200 g of toluene for 2.5 hours in a water separator. After cooling, the mixture is washed with sodium carbonate solution and dried over sodium sulfate. 3 g of sodium carbonate are added and the mixture is distilled on a 20 cm packed column. At 122-132OC/2.3-2.1 mbar this yields 99 g of product comprising 54% of isomer 1 and 8.3% of isomer 2 and containing other isomers with double bonds.

Odour: plum, fig, apricot, damascone, pleasantly fruity-sweet combination

For the structural determination the isomers 1 and 2 were separated by high performance liquid chromatography and analysed by means of NMR spectroscopy.

2-[1-Methyl-3-(2,6,6-trimethyl-1-cyclohexen-1-yl)-allyl]-1,3-dioxolane (isomer 1)

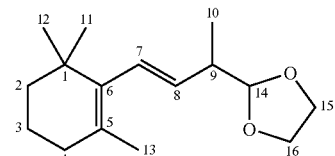

| δ (ppm) | | | J (Hz) | |
|---|---|---|---|---|
| 0.980 | s | 3 H | | CH3 (11 or 12) |
| 0.982 | s | 3 H | | CH3 (11 or 12) |
| 1.10 | d | 3 H | 7.0 | CH3 (10) |
| 1.43 | m | 2 H | | CH2 (2) |
| 1.59 | m | 2 H | | CH2 (3) |
| 1.67 | q | 3 H | 0.9 | CH3 (13) |
| 1.96 | t br | 2 H | 6.4 | CH2 (4) |
| 2.50 | ddqd | 1 H | 1.1/4.1/6.9/8.0 | CH (9) |
| 3.86 | m | 2 H | | CH2 (15, 16) |
| 3.95 | m | 2 H | | CH2 (15, 16) |
| 4.77 | d | 1 H | 4.2 | CH (14) |
| 5.36 | dd | 1 H | 7.8/16.0 | CH (8) |
| 5.91 | d br | 1 H | 16.0 | CH (7) | solvent: $CDCl_3$
internal standard: tetramethylsilane (TMS)
frequency: 400 MHz

2-[1-Methyl-3-(2,6,6-trimethyl-1-cyclohexen-1-yl)-propenyl]-1,3-dioxolane (isomer 2)

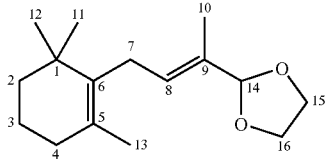

| δ (ppm) | | | J (Hz) | |
|---|---|---|---|---|
| 0.96 | s | 6 H | | 2 *CH3 (11, 12) |
| 1.42 | m | 2 H | | CH2 (2) |
| 1.53 | s br | 3 H | | CH3 (13) |
| 1.57 | m | 2 H | | CH2 (3) |
| 1.67 | dt | 3 H | 1.4/1.1 | CH3 (10) |
| 1.91 | t | 2 H | 6.3 | CH2 (4) |
| 2.78 | d | 2 H | 6.4 | CH2 (7) |
| 3.90 | m | 2 H | | CH2 (15, 16) |
| 4.01 | m | 2 H | | CH2 (15, 16) |
| 5.08 | d | 1 H | 0.6 | CH (14) |
| 5.48 | dqt | 1 H | 0.6/1.4/6.4 | CH (8) | solvent: CDCl$_3$
internal standard: tetramethylsilane (TMS)
frequency: 400 MHz b) Reaction parameters: entraining agent: toluene; amount of p-toluenesulfonic acid=0.15 g
  Molar ratio 2-methyl-4-(2,6,6-trimethyl-1-cyclohexen-1-yl)-2-butenal:ethylene glycol=1:3
  103 g (0.5 mol) of 2-methyl-4-(2,6,6-trimethyl-1-cyclohexen-1-yl)-2-butenal, 93 g (1.5 mol) of ethylene glycol and 0.15 g of p-toluenesulfonic acid are heated with 200 g of toluene for 2.5 hours in a water separator, 39 g of a water/ethylene glycol mixture being separated off. After cooling, the mixture is washed with sodium carbonate solution and dried over sodium sulfate. 3 g of sodium carbonate are added and the mixture is distilled on a 30 cm packed column to give 103 g of product comprising 26% of isomer 1 and 43% of isomer 2.
  Odour: as indicated under a), but less impact and character c) Reaction parameters: entraining agent: cyclohexane; amount of p-toluenesulfonic acid=1 g
  Molar ratio 2-methyl-4-(2,6,6-trimethyl-1-cyclohexen-1-yl)-2-butenal:ethylene glycol =1:3
  103 g (0.5 mol) of 2-methyl-4-(2,6,6-trimethyl-1-cyclohexen-1-yl)-2-butenal, 93 g (1.5 mol) of ethylene glycol and 1 g of p-toluenesulfonic acid are heated with 200 g of cyclohexane for 14 hours in a water separator. After cooling, the mixture is washed with sodium carbonate solution and dried over sodium sulfate. 2.6 g of sodium carbonate are added and the mixture is distilled on a 20 cm packed column to give 90 g of product comprising 43% of isomer 1 and 22% of isomer 2.

d) Reaction parameters: entraining agent: toluene; amount of p-toluenesulfonic acid=1 g
  Molar ratio 2-methyl-4-(2,6,6-trimethyl-1-cyclohexen-1-yl)-2-butenal:ethylene glycol=1:1.3
  103 g (0.5 mol) of 2-methyl-4-(2,6,6-trimethyl-1-cyclohexen-1-yl)-2-butenal, 40.3 g (0.65 mol) of ethylene glycol and 1 g of p-toluenesulfonic acid are heated with 200 g of toluene for 2.5 hours in a water separator, 25 g of a water/ethylene glycol mixture being separated off. After cooling, the mixture is washed with sodium carbonate solution and dried over sodium sulfate and the toluene is distilled off on a rotary evaporator. 98.5 g of crude product containing 58.5% of isomer 1 and 7.8% of isomer 2 are then distilled off on a thin film evaporator (jacket temperature=197° C., pressure =1.6 mbar) at a top temperature of 125-140° C. 3 g of sodium carbonate are added to the crude distillate and the mixture is distilled on a 20 cm packed column. At 121-125° C./1.5-1.9 mbar this yields 65 g of product comprising 72% of isomer 1 and 8.4% of isomer 2 and containing other isomers with double bonds.

e) Transisomerization
  13 g of an isomer mixture containing 26% of isomer 1 and 52% of isomer 2 are refluxed for 15 hours with 0.1 g of p-toluenesulfonic acid in 20 g of toluene. After cooling, the mixture is washed with sodium carbonate solution and dried over sodium sulfate. 9.5 g of isomer mixture comprising 70% of isomer 1 and 7.5% of isomer 2 are obtained by means of bulb tube distillation.

Example 2

Preparation of an isomer mixture containing 2-[1-methyl-3-(2,6,6-trimethyl-1-cyclohexen-1-yl)allyl]-1,3-dioxane as the main component 103 g (0.5 mol) of 2-methyl-4-(2,6,6-trimethyl-1-cyclohexen-1-yl)-2-butenal, 38 g (0.5 mol) of 1,3-propanediol and 1 g of p-toluenesulfonic acid are heated with 200 g of toluene for 2.5 hours in a water separator. After cooling, the mixture is washed with soda solution and dried over sodium sulfate. 3 g of sodium carbonate are added and the mixture is distilled on a 30 cm packed column. At 122-126° C./1.6-0.82 mbar this yields 81 g of product comprising 66% of 2-[1-methyl-3-(2,6,6-trimethyl-1-cyclohexen-1-yl)allyl]-1,3-dioxane and also containing other isomers with double bonds.

Odour: plum, fig, iris, lovage, tea, spicy
The structure was determined by means of NMR spectroscopy.

2-[1-Methyl-3-(2,6,6-trimethyl-1-cyclohexen-1-yl)-allyl]-1,3-dioxane

| δ (ppm) | | | J (Hz) | |
|---|---|---|---|---|
| 0.97 | s | 3 H | | CH3 (11 or 12) |
| 0.98 | s | 3 H | | CH3 (11 or 12) |
| 1.07 | d | 3 H | 6.9 | CH3 (10) |
| 1.31 | d br | 1 H | 13.3 | CH (16) |
| 1.43 | m | 2 H | | CH2 (2) |
| 1.58 | m | 2 H | | CH2 (3) |
| 1.67 | q | 3 H | 0.9 | CH3 (13) |
| 1.95 | t | 2 H | 6.3 | CH2 (4) |
| 2.06 | ttd | 1 H | 5.1/12.4/13.3 | CH (16) |
| 2.41 | dqd | 1 H | 4.9/6.9/8.0 | CH (9) |
| 3.74 | dt | 2 H | 2.6/12.1 | CH2 (15, 17) |
| 4.11 | m | 2 H | | CH2 (15, 17) |

-continued

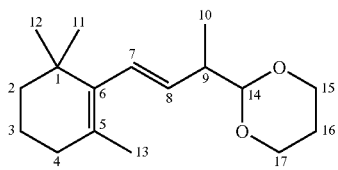

| δ (ppm) | | | J (Hz) | |
| --- | --- | --- | --- | --- |
| 4.36 | d | 1 H | 4.9 | CH (14) |
| 5.36 | dd | 1 H | 8.0/16.0 | CH (8) |
| 5.87 | d br | 1 H | 16.0 | CH (7) | solvent: $CDCl_3$
internal standard: tetramethylsilane (TMS)
frequency: 400 MHz

Example 3

Fragrance composition according to the invention compared with a base composition:

3.1 Base composition:

| | Parts by weight |
| --- | --- |
| Aldehyde C7 50% in PEA | 1 |
| Aldehyde C8 | 0.7 |
| Aldehyde C9 | 1.2 |
| Aldehyde C10 | 1.5 |
| Alcohol C6 kosher | 2 |
| Beeswax abs. | 2 |
| Citral FF | 8 |
| Citronellal supra | 0.9 |
| Citronellol laevo | 135 |
| Citronellyl acetate extra | 5 |
| Citronellyl formate | 2 |
| Lemon oil terpenes WONF | 2 |
| Dipropylene glycol | 518.1 |
| Estragole | 7 |
| Ethyl heptylate | 1 |
| Ethyl ricinoleate | 15 |
| Eugenol | 2 |
| Farnesol 100% | 3 |
| Geranitrile | 20 |
| Geranium oil Bourbon | 10 |
| Geranyl formate supra | 1 |
| Linalool | 5 |
| Myristic acid | 10 |
| Nonyl acetate | 2 |
| 1-Octyl acetate | 2 |
| Phenylacetaldehyde 50% DPG 2% DPG | 5 |
| Phenylethyl acetate | 15 |
| Phenylethyl formate | 4 |
| Propylad | 10 |
| Rose oxide L | 0.3 |
| Terpinen-4-ol nat. | 0.3 |
| Tetrahydrogeraniol | 8 |

3.2 The addition of 200 g of the product of Example 1 to the base composition according to 3.1 creates a fresh, natural and pleasant blossom effect. The fruity elements have a rounding-off and feminine effect, resulting in a gentle harmony.

The invention claimed is:

1. Acetal of formula I:

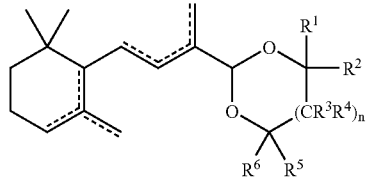

in which
the radicals $R^1$ to $R^6$ independently of one another are each hydrogen, methyl, ethyl, n-propyl, isopropyl, n-butyl, isobutyl, sec-butyl or tert-butyl,
n=0 or 1, and
there is a single bond or double bond at the location of a broken line between two C atoms,
any double bond present in the chain linking the aliphatic ring to the acetal group having the E or Z configuration,
with the proviso that
the number of double bonds incorporating a C atom of the aliphatic ring is 0 or 1, and
the number of double bonds not incorporating a C atom of the aliphatic ring is 0 or 1.

2. Acetal according to claim 1 in which the radicals $R^1$ to $R^6$ independently of one another are each hydrogen or methyl.

3. Acetal according to claim 1 which has formula IA or IB below:

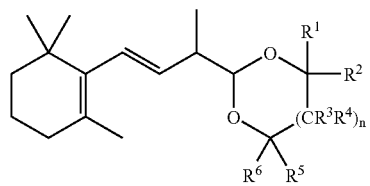

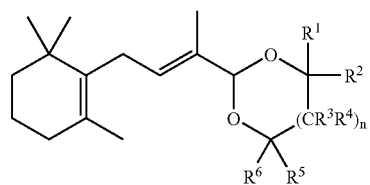

the double bond in the chain linking the aliphatic ring to the acetal group having the E or Z configuration in each case.

4. Acetal according to claim 3 which is 2-[1-methyl-3-(2,6,6-trimethyl-1-cyclohexen-1-yl)allyl]-1,3-dioxolane
or
2-[1-methyl-3-(2,6,6-trimethyl-1-cyclohexen-1-yl)propenyl]-1,3-dioxolane.

5. Acetal according to claim 1 which can be prepared by the acetalization of 2-methyl-4-(2,6,6-trimethyl-1-cyclohexen-1-yl)-2-butenal.

6. Mixture of two or more acetals according to claim 1.

7. Enhancing a composition by adding thereto one or more acetals according to claim 1 (a) as a fragrance, or (b) for the preparation of a mixture of fragrances or a perfume.

8. Product comprising
a carrier or a substrate, and a sensorially effective amount, in direct contact therewith, of one or more acetals according to claim 1.

9. Product according to claim 8 selected from the group comprising alcoholic perfumes, body care products and household cleaning or care products.

10. Product according to claim 9, characterized in that the body care products are selected from the group comprising soaps, shower gels, shampoos, bath additives, skin creams, body lotions and deodorants, and the cleaning products are selected from the group comprising detergents, fabric softeners, air purifiers and cleaners.

11. Process for the preparation of an acetal according to claim 1,
wherein 2-methyl-4-(2,6,6-trimethyl-1-cyclohexen-1-yl)-2-butenal is reacted with an aliphatic 1,2- or 1,3-diol under acid catalysis and water separation.

12. Process according to claim 11 wherein water formed in the reaction is removed by (a) distillation, b) azeotropic distillation, or (c) azeotropic distillation together with an entraining agent.

* * * * *